(12) United States Patent
Korotko et al.

(10) Patent No.: US 7,153,273 B2
(45) Date of Patent: Dec. 26, 2006

(54) BLOOD-FLOW-OCCLUDING, TEMPERATURE-SENSING CATHETERS AND METHODS OF USE

(75) Inventors: Joseph R. Korotko, Livonia, MI (US); Dan Carroll, Ann Arbor, MI (US); William W. O'Neill, Grosse Pointe Farms, MI (US)

(73) Assignee: Accumed Systems, Inc., Ann Arbor, MI (US)

( * ) Notice: Subject to any disclaimer, the term of this patent is extended or adjusted under 35 U.S.C. 154(b) by 117 days.

(21) Appl. No.: 10/401,927

(22) Filed: Mar. 28, 2003

(65) Prior Publication Data
US 2003/0233033 A1    Dec. 18, 2003

Related U.S. Application Data

(63) Continuation-in-part of application No. 09/882,889, filed on Jun. 15, 2001, now Pat. No. 6,712,771.

(60) Provisional application No. 60/444,497, filed on Feb. 3, 2003, provisional application No. 60/376,250, filed on Apr. 29, 2002, provisional application No. 60/211,995, filed on Jun. 16, 2000.

(51) Int. Cl.
A61B 5/00    (2006.01)

(52) U.S. Cl. ..................................... 600/549

(58) Field of Classification Search ................ 600/474, 600/549, 393, 505, 434, 435, 481, 585; 374/141, 374/148, 166, 179
See application file for complete search history.

(56) References Cited

U.S. PATENT DOCUMENTS 5,433,708 A * 7/1995 Nichols et al. ............. 604/113

6,245,026 B1 * 6/2001 Campbell et al. ........... 600/549
6,579,243 B1 * 6/2003 Kokate et al. .............. 600/549
6,615,071 B1 * 9/2003 Casscells et al. ........... 600/474
6,712,771 B1 * 3/2004 Haddock et al. ............ 600/549

OTHER PUBLICATIONS

Naghavi et al., "Thermosensor Catheter; a Nitinol Shape Memory Basket Catheter to Measure Temperature of Vessel Wall With Continuous Blood Flow", Journal of the American College of Cardiology, Feb. 2000.*

* cited by examiner

*Primary Examiner*—Max F. Hindenburg
*Assistant Examiner*—Brian Szmal
(74) *Attorney, Agent, or Firm*—Gifford, Krass, Groh, Sprinkle, Anderson & Citkowski, PC (57) ABSTRACT

A catheter assembly for sensing the temperature of an arterial wall or other body lumen includes a blood-flow-occluding feature to increase the accuracy of the temperature measurements. In addition to the flow-occluding feature, the catheter includes a distal end with a temperature sensing structure and a proximal end including a manually operated expansion control. The temperature sensing structure including one or more presentation elements in the form of a basket or braided structure having at least one temperature sensor supported thereon, each sensor being operative to generate an electrical signal indicative of temperature. The presentation elements are physically coupled to the manually operated expansion control, such that operation of the control causes the structure to move between a collapsed state, enabling the temperature sensing structure to be positioned in a section of the vessel to be measured, and an expanded state, wherein the sensor is in contact with, or immediately proximate to, the vessel wall.

7 Claims, 12 Drawing Sheets

BLOOD-FLOW-OCCLUDING, TEMPERATURE-SENSING CATHETERS AND METHODS OF USE

REFERENCE TO RELATED APPLICATIONS

This application claims priority from U.S. Provisional Patent Application Ser. No. 60/376,250, filed Apr. 29, 2002 and 60/444,497, filed Feb. 3, 2003, and is also a continuation-in-part of U.S. patent application Ser. No. 09/882,889, filed Jun. 15, 2001, now U.S. Pat. No. 6,712,771, which claims priority from U.S. Provisional Patent Application Serial No. 60/211,995, filed Jun. 16, 2000. The entire content of each application and patent is incorporated herein by reference.

FIELD OF THE INVENTION

This invention relates generally to medical instrumentation and appliances and, in particular, to temperature sensing catheters and methods of use.

BACKGROUND OF THE INVENTION

Arteriosclerosis is a major source of adult morbidity and mortality in industrialized countries. The condition may lead to a number of complications, including coronary thrombosis, myocardial ischemia, unstable angina, myocardial infarction and restenosis of stents and bypass grafts. The classification of atherosclerotic lesions by type can be valuable in predicting clinical complications, and the type of plaque is likely a better predictor of cardiovascular events than angiographic data.

Unstable plaque is well established as producing high risk for sudden myocardial infarction, either through plaque rupture and subsequent thrombotic response, or thrombosis generated at the inflamed surface of the plaque. The rupture of unstable plaque, and the subsequent generation of thrombus, has been estimated to account for 60 to 70 percent of fatal myocardial infarctions and up to 85 percent of all myocardial infarctions.

Unstable plaque is characterized by a lipid-rich core, chronic inflammation, thin fibrous cap, and activated macrophages. Angiography can identify the presence of a ruptured plaque after rupture, but not before rupture. Thus, it cannot determine the risk associated with a given plaque.

Due to chronic inflammation, the temperature of unstable plaque is typically elevated above that of the adjacent sites on the inner lumen of the vessel. Extensive research has been conducted to confirm the elevated temperatures of unstable plaques, and to develop techniques to clinically identify them. It has been found that there is a correlation between the temperature of atherosclerotic plaque and the vulnerability to blood vessel rupture. In particular, it has been determined that inflamed, unstable deposits typically give off more heat than do healthy, non-inflamed tissues. Accordingly, there have been various apparatus and methods proposed to monitor the temperature of the vessel wall without occluding blood flow. U.S. Pat. Nos. 5,871,449; 5,924,997; and 5,935,075 provide background with regard to the general approach.

To determine that thrombotic events could be predicted through thermal measurements on the plaque surface, Willerson et al. measured the intimal surface temperatures on 20 sites located on 50 samples of excised living carotid artery samples from 48 patients using a thermistor, and then conducted histological studies. The results showed 37% of plaque regions warmer by up to 2.2° C. These warmer regions could not be distinguished from cooler regions by visual observation, but correlated positively with cell density, a marker of inflammation.

Stefanadis et al. conducted human in vivo measurements of plaques using a Betatherm Microchip NTC 100K6 MCD368, 0.457 mm diameter thermistor on the end of a guide wire pressed against the vessel wall by a hydrofoil. They measured thermal heterogeneity of plaque temperatures repeatedly with an accuracy of 0.05° C. and spatial and temporal resolutions of 500 um and 300 ms, in 90 patients with normal coronary arteries, stable angina, unstable angina, and with acute myocardial infarction. This group found artery-wall temperatures that increased progressively from normal patients, to stable angina patients, to unstable angina patients. The measurement of temperature differences in the inner lumen of coronary arteries shows great promise for identifying sites of unstable plaque.

Research on classification of plaque as stable or unstable has been carried out in three main areas: thermal, Ultra-Fast Magnetic Resonance Imaging (MRI) and Intravascular Ultrasound (IVUS), with some work on a few others (e.g. Raman scattering, elastography, optical coherence tomography). While MRI and IVUS show promise, only thermal techniques offer a direct, inexpensive method of plaque classification that, due to its minimal hardware and disposable requirements, can be quickly and inexpensively implemented.

Plaque classification by MRI presents numerous obstacles. It brings the problems of requiring a special machine, typically located in other regions of the facility and not available on an ad hoc basis, into the cath lab as questions of plaque stability may arise. The ability of MRI to characterize human atherosclerotic plaque has been investigated by comparing MRI images of carotid artery plaque with histologic examination of the specimens after carotid endarterectomy. The studies indicated that MRI can discriminate the presence of a lipid core and fibrous cap in the carotid artery. The ability of MRI to characterize plaque composition of coronary arteries in the beating human heart has not been demonstrated. Even if the technical challenges of spatial and temporal resolution are solved, the cost of imaging coronary arteries using MRI is likely to be substantial.

While IVUS can accurately identify arteriosclerosis in its early stages, it is much less effective in the classification of plaque by type. Further, IVUS requires expensive and large equipment that also must be brought into the cath lab when needed. The main limitation of IVUS is cost. IVUS enjoys an installed base in many cath labs, unlike other competing technologies to classify plaque, but it is problematic in this application. IVUS is very operator dependent and typically has a 300 micron resolution, the thickness of the fibrous cap on unstable plaque. Thus, IVUS does not have the needed resolution to identify unstable plaque. Although numerous clinical studies have been performed with IVUS, there are very limited follow-up data to suggest that IVUS examination of a coronary artery can be used to predict the probability that a plaque will rupture.

Yamagishi et al. performed IVUS examination of 114 coronary plaques in 106 patients. During an average follow-up period of 22 months, 12 patients had an acute coronary event related to a plaque that was previously examined by IVUS. Ten of the 12 plaques contained an echolucent zone consistent with a lipid-rich core. Only 4 of 90 sites not associated with acute events had an echolucent zone ($p<0.05$).

Optical Coherence Tomography (OCT) has problems due to its limited penetration distance, and the fact that it requires a saline flush to remove blood from the area and permit transmission of the optical radiation. Further, it can run only at ~5 frames/sec., which does not provide adequate temporal resolution. This technique, and others, such as pulsed laser radiation and the use of Raman scattering spectroscopy, require the vessel be purged of blood with clear saline for the signals to propagate. Further, they are much less developed than other techniques.

Classification of atherosclerotic plaque stability by measurement of its surface temperature is direct. Due to the chronic inflammation, the surface temperature of unstable plaque is typically elevated above that of the adjacent sites on the inner lumen of the vessel. Measurements in vivo and ex vivo have been made of active plaque sites, with temperature differences from the adjacent normal artery wall ranging up to 2 to 3° C. The equipment associated with thermal measurements may be small and inexpensive, thus easily portable between cath labs or available in all cath labs in a single facility, as opposed to Magnetic Resonance Imaging (MRI) and Intravascular Ultrasound (IVUS). Identification of unstable plaques would permit the cardiologist to decide on treatment on a site-by-site basis during a single catheter insertion.

There are numerous potential treatments for these unstable lesions, including anti-inflammatory and/or anti-microbial treatments, aggressive cholesterol lowering, and heating to generate apoptosis. Stenting techniques are influenced by the classification of the plaque being treated. As classification of plaques becomes established, other therapeutic techniques will no doubt develop.

While plaque temperature measurement and catheters therefore showed early promise in terms of early diagnosis and treatment, it has more recently been discovered that the temperature elevation to be identified as representative of unstable lesions is complicated by the "cooling affect" of blood flow. In particular, a recent paper by Stefanadis, entitled *Thermal Heterogeneity in Stable Human Coronary Atheroschlerotic Plaques is Underestimated in Vivo: The "Cooling Effect" of Blood Flow* postulates that the "cooling effect" of blood flow may lead to an underestimation of in vivo temperature measurements associated with atheroschlerotic plaques.

Accordingly, the need remains for an improved system and method for analyzing plaque tissues exhibiting an elevated temperature, both to predict rupture or other clinical events.

SUMMARY OF THE INVENTION

This invention improves upon the existing art by providing a catheter assembly for sensing the temperature of an arterial wall or other body lumen, the assembly including a blood-flow-occluding feature to increase the accuracy of the temperature measurements. In addition to the flow-occluding feature, the catheter includes a distal end with a temperature sensing structure and a proximal end including a manually operated expansion control. The temperature sensing structure includes one or more presentation elements, preferably in the form of a basket or braided structure having at least one temperature sensor supported thereon, each sensor being operative to generate an electrical signal indicative of temperature. The presentation elements are physically coupled to the manually operated expansion control, such that operation of the control causes the structure to move between a collapsed state, enabling the temperature sensing structure to be positioned in a section of the vessel to be measured, and an expanded state, wherein the sensor is in contact with, or immediately proximate to, the vessel wall.

In the preferred embodiment, the feature to occlude blood flow is an inflatable balloon disposed near the temperature-sensing structure, preferably in the form of an expandable basket or braid structure. The temperature sensors are preferably thermistors, and an elastic sleeve covering the expandable basket or braid structure is also preferably provided to further insulate the temperature sensors and provide structural strength. At least one thermal sensor may optionally be provided to measure a non-wall temperature.

The sensors are interfaced to a data unit operative to receive signals from the sensors and display information indicative of vessel wall temperature. Each sensor may be independently wired to the data unit or signal multiplexing may be used.

A more robust catheter assembly according to the invention includes an outer tube having a proximal end intended to remain outside a patient and a distal end terminating in an inflatable balloon to occlude blood flow and an inner tube disposed co-extensively within the outer tube. The inner tube extending to a distal tip beyond the distal end of the outer tube, and an expandable basket or braid structure having a first end attached to the distal tip of the inner tube and a second end attached to a guide wire slidingly disposed within the inner tube to an expansion control at the proximal end.

The expandable basket or braid structure includes one or more temperature sensors supported thereon, each sensor being operative to generate an electrical signal indicative of temperature, such that operation of the expansion control causes the structure to move between a collapsed state, enabling at least one of the sensors to be positioned in a section of the vessel to be measured, and an expanded state, wherein the sensor is in contact with, or immediately proximate to, the vessel wall while the flow of blood is occluded.

Given the independent control of the temperature-sensing structure and blood-occluding feature, a method unique to this invention permits a particular point being analyzed to serve as its own baseline reference. According to this aspect of the invention, the catheter is inserted into an area to be analyzed, and the presentation elements are expanded such that the temperature sensors contact one or more points of the vessel wall. The electrical signals from the sensors are read out to the data box and stored and/or displayed, these being indicative of wall temperature with at least a portion of blood flow being present. After this measurement is taken, the occluder feature is activated to interrupt or stop blood flow, at which point the signals from the sensors are monitored to determine temperature rise, if any, as well as the difference between the temperature sensed during at least partial flow and that with stagnant fluid. This results in a much more accurate determination of $\Delta T$, defined as $T_{occluded} - T_{flowing}$.

Unique to this method, the method may further include the steps of collapsing the basket or braided structure; moving the temperature-sensing up to a different location; and expanding the basket or braided structure to perform an additional temperature reading while the flow of blood remains occluded. In such a case, it may be advantageous to use an initial measurement with at least partial blood flow to serve as a baseline temperature measurement of the subsequent readings taken while the flow of blood is partially or fully occluded.

The method may further include the step of choosing a therapeutic technique as a function of the sensed temperature. For example, the therapeutic technique may involve the selection of a stent to minimize restenosis, including the choice between the drug-coated versus non-drug-coated stent.

DETAILED DESCRIPTION OF THE INVENTION

This invention resides in a thermal sensing catheter (TSC) operative to perform localized temperature measurements with respect to a human or animal arterial or other vessel wall. The embodiments find particular utility in predicting whether a section of a body lumen undergoing stenting as a treatment for stenosis will likely be subject to restenosis. If such is the case, alternative approaches to the stenting procedure (i.e., length/diameter, coated/medicated) may be elected as appropriate. The instrument and methods are also valuable to other diagnoses, including plaque assessment, including plaque stability, not available with current technology.

In terms of apparatus, in the preferred embodiments, miniaturized temperature sensors in the form of microthermistors are embedded into or supported relative to a plurality of expandable presentation elements disposed at the distal end of a catheter. The sensors may then be deployed to measure the surface temperature of the inner wall of coronary arteries at multiple sites to identify sites conducive to restenosis or exhibiting an elevated temperature indicative of unstable plaque.

In the preferred embodiment, the presentation elements are disposed relative to an expandable braided structure that is actively caused to collapse and expand. A control mechanism located at the proximal end of the catheter outside the body is used to expand and collapse the structure as further described below. In one disclosed example, a dedicated guide wire coupled to the control mechanism is used to pull on the distal-most end of the braid elements, causing it to shorten along its length and to expand out radially. When the guide wire is pushed, the ends of the structure are pulled apart, causing the braid to collapse.

The control mechanism preferably forms part of a battery-powered, hand-held data box including a port to which the catheter assembly connects, thereby making electrical contact for ground and the signal lines of each of the individual sensors. The connections from each sensing element are preferably separate and dedicated; however, in an alternative configuration, multiplexing may be used to reduce the number of signal wires.

The data box includes a display to present the calibrated readings from the sensors, as well as memory capabilities to store data for later download through a port incorporated in the housing. The output of the data box may be provided to a computer, to permit full-screen display of the thermal data. In either mode, a full recording of a procedure may be saved for later analysis.

The braid structure can be made from any of a variety of biocompatible materials, including polymers and metallic compositions, such as stainless steel or nitinol. The strands used to make the braid may have a round cross section, like a wire, or they could be square, rectangular or some other geometric shape so long as they serve the purposes of the expansion and contraction.

Figure 1:
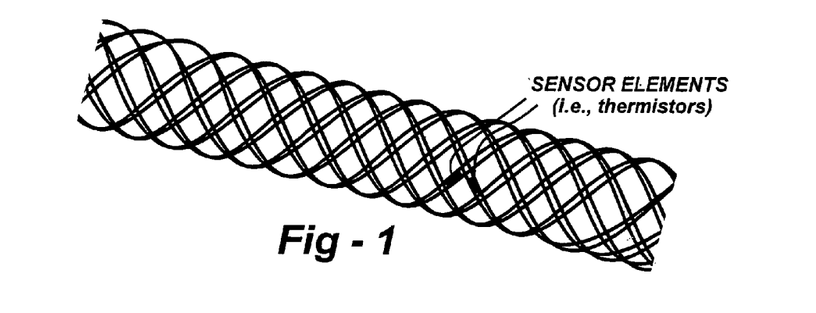
FIG. 1 is a rendering of a structure wherein temperature sensors are integrated into a braided structure according to the invention.
Figure 2:
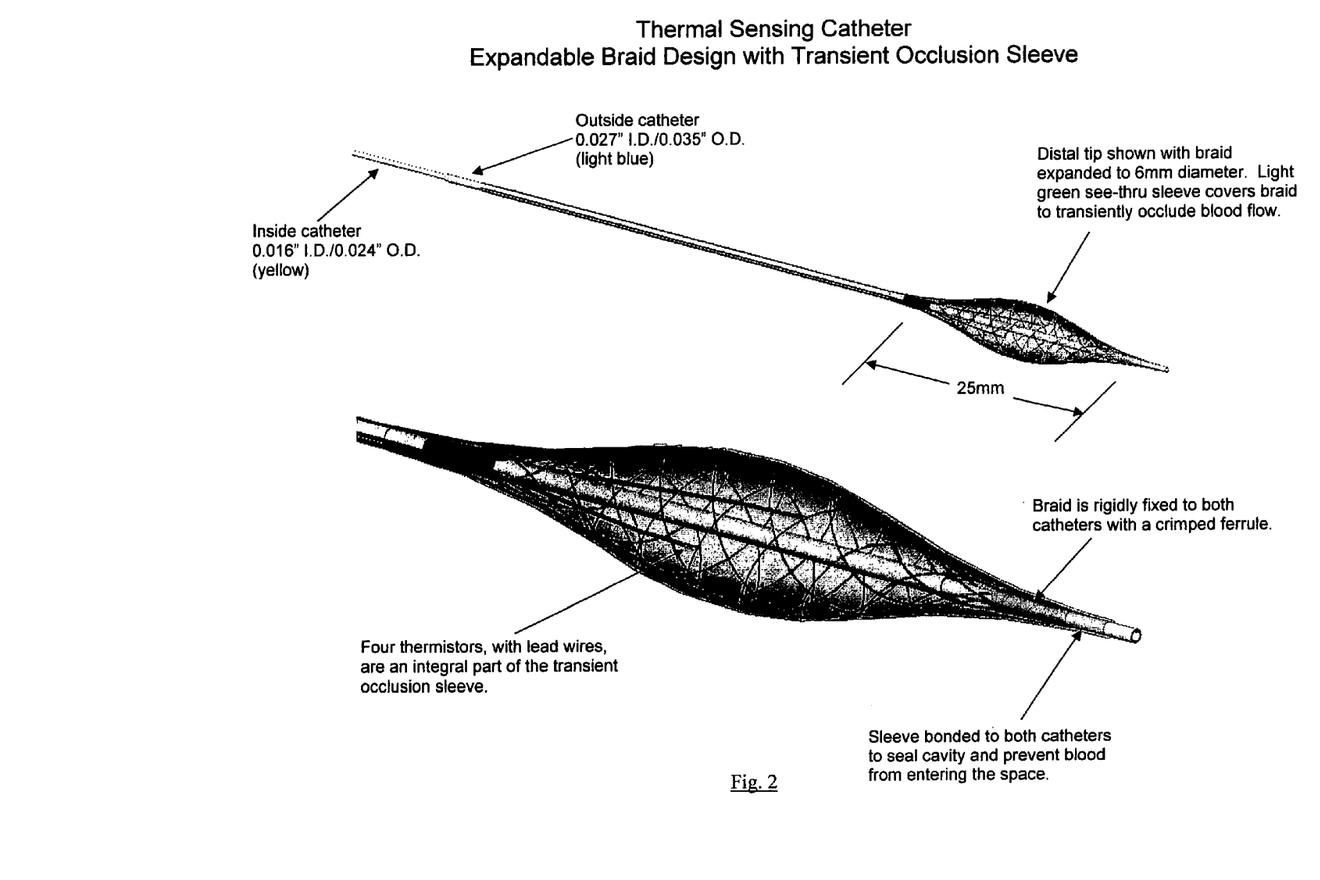
FIG. 2 shows a braided structure and elastic cover.

As an option to the placement of the temperature sensors on the braid structure, they may be made an integral part of the braid itself, as shown in FIG. 1. This may be accomplished by weaving the sensors into the braid, in which case the electrical lead wires associated with the sensing elements may replace some of the regular strands in the braid. Alternately, the lead wires may be attached to strands before they are woven into the braid construction. As a further alternative, as discussed below, if an elastic sleeve covering is used over the structure, the sensors may be disposed on or in the covering as shown in FIG. 2. In all cases, the sensors move with the braid. That is, when the structure is dilated and makes contact with the wall, the sensors will also make contact with, or at least become immediately proximate to, the vessel wall. Conversely, when the braid collapses to a low profile state, the sensors are also positioned away from the inner wall of the body lumen.

In other respects the catheter may be generally similar to other diagnostic or interventional catheters. Its length, construction, flexibility, and size (diameter) would all be appropriate for the application. For example, if the invention were to be used for a cardiac catheterization, it might be 130–150 cm long, constructed of flexible polymers, contain a central guide wire lumen, and be about 6F (2 mm diameter) or smaller in order to pass through a guide catheter. The catheter would also preferably include a y-connector with standard luer fittings on the proximal end to interface with other devices. If the braid structure is not otherwise radiopaque, a radiopaque marker may be included so the sensing element may be located with fluoroscopy.

In use, the braided end of the catheter is in a collapsed state while it is inserted and positioned in a vessel. Once properly positioned, the braid can be expanded so that the thermal sensing elements make contact with the vessel wall. The braid can be designed so that it makes a gentle atraumatic contact. This is important to prevent, or minimize, damage to the vessel.

There are several advantages to this approach. First, the device provides an efficient means for expanding a structure in a vessel and making contact with the wall. The braid will make gentle contact with the wall and cause little or no damage. While it is expanded, it will allow for blood flow and not occlude the vessel. It will conform to the topography of the vessel and maintain contact if the catheter is moved. Moreover, with the use of an elastic sleeve, a more uniform arrangement of the sensors is maintained around the circumference of the artery or other vessel. As perhaps best seen in FIG. 7E, the use of a braid and sleeve facilitates intimate contact around the entire circumference of the inside of the vessel, even if it is non-round in shape.

As discussed in the Background of the Invention, it has recently been demonstrated that the "cooling effects" due to blood flow may adversely affect the ability of a temperature-sensing catheter to conduct accurate in vivo estimates of temperature. To investigate this hypothesis, an experiment was undertaken to determine the extent to which a flowing liquid inhibits the ability to conduct accurate measurements of vessel wall temperatures. The experimental set up, shown in FIG. 3, broadly uses a pair of canulated tubes, which engage with each other at a point of contact in cris-crossing fashion. A first tube 402 carries unheated water. A metal (brass) tube 404 touching the water-carrying tube in a localized area 418 carries heated water. This second tube 404 in turn creates a small localized spot 418 on the wall of the first tube 402 which is higher in temperature than the rest of the tube 402 or the unheated water passing through it.

Figure 3:
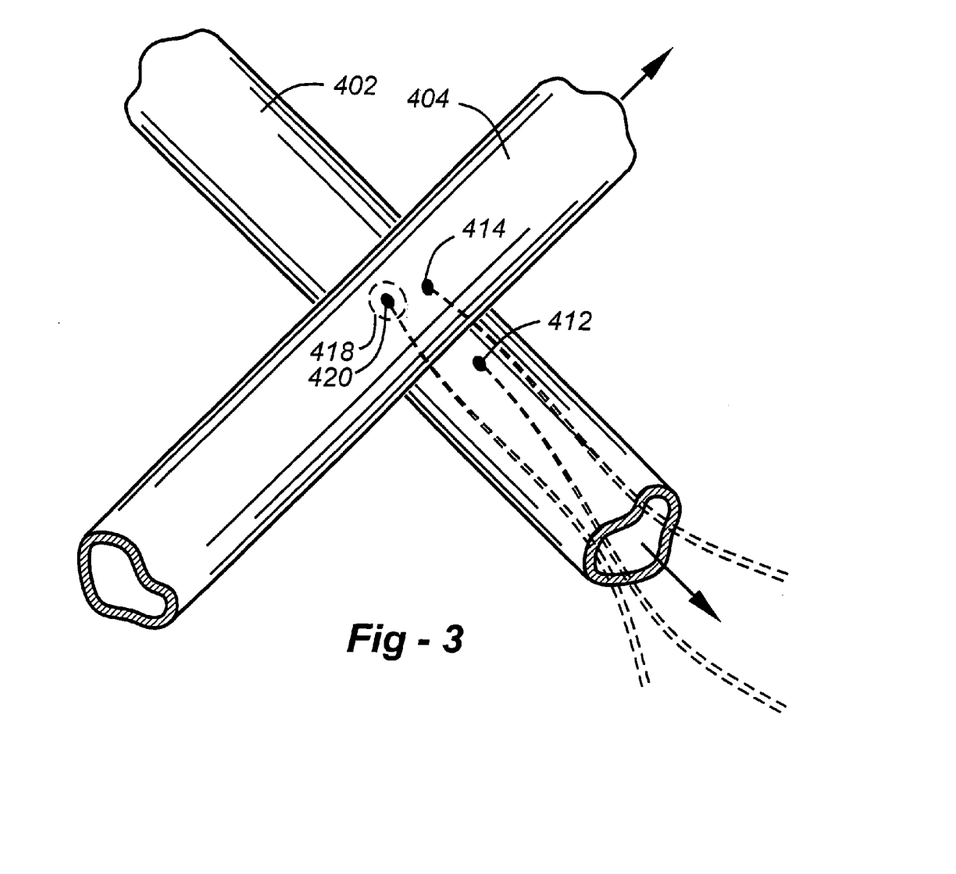
FIG. 3 is a perspective, simplified view of an experimental set up used to demonstrate that, indeed, the cooling effect of blood flow adversely affects the ability of a temperature sensing catheter to obtain an accurate reading.

Three miniature temperature sensors were used, including a first temperature sensor 412 used to measure the temperature of the flowing unheated water (Tw), a second sensor 414 used to measure the wall temperature inside of the tube 402 (Tt), and a third temperature sensor 420 within the unheated water carrying tube to measure the point of contact with the brass tube carrying the heated water (Tc).

Figure 4:
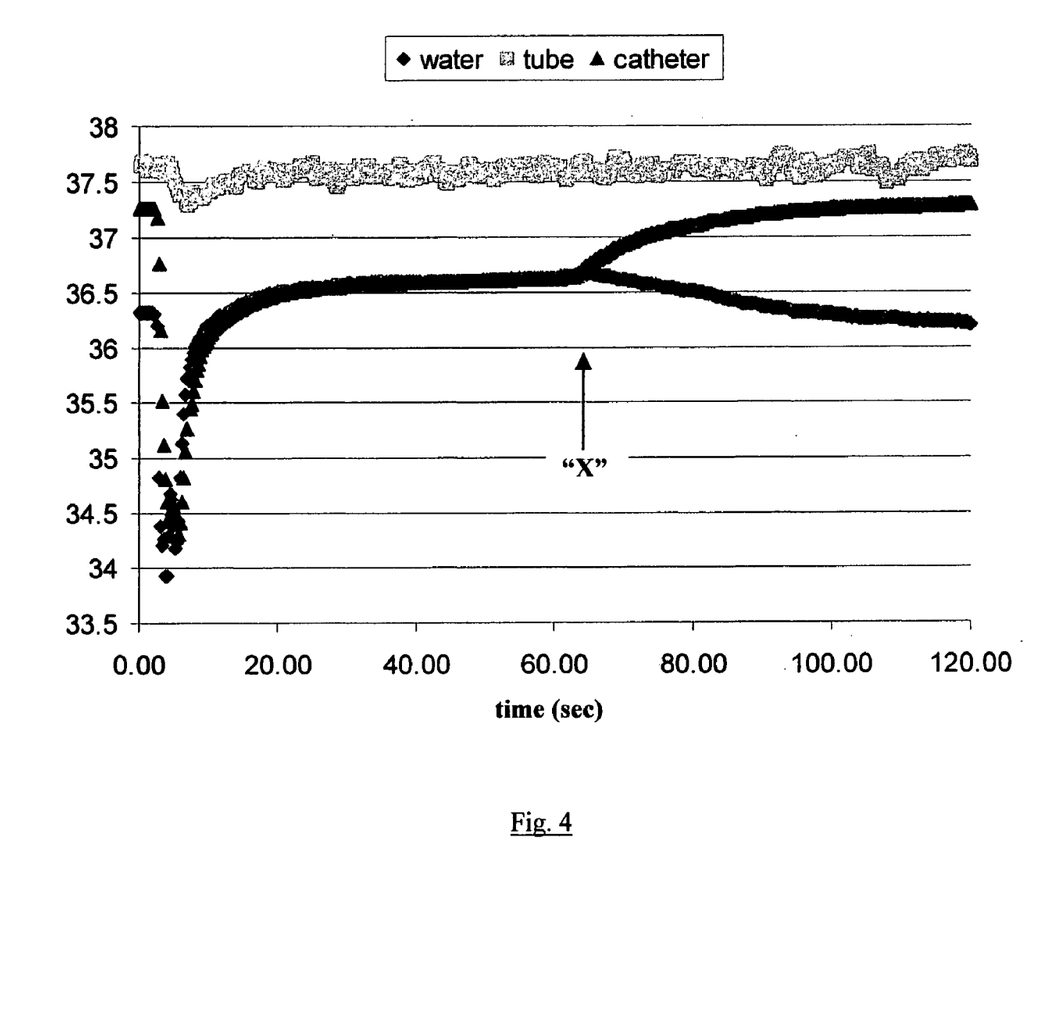
FIG. 4 illustrates how, by occluding the flow of a liquid around a temperature sensor, a more accurate reading may be obtained.

The results of these experiments are shown in FIG. 4. Note that Tw and Tc generally track one another until a point X, wherein the curves depart from one another. It is at this point that the flow through the non-heated water carrying tube is occluded. When this occurs, it will be seen that the difference between Tc and Tt transitions from being relatively large to much smaller, as the curve representative of Tc begins to approach Tt beginning at the point X. This confirms the fact that while non-occluding temperature sensing catheters may be useful in some cases, a more accurate reading of elevated vessel wall temperature may be obtained by occluding blood flow.

Figure 5A:
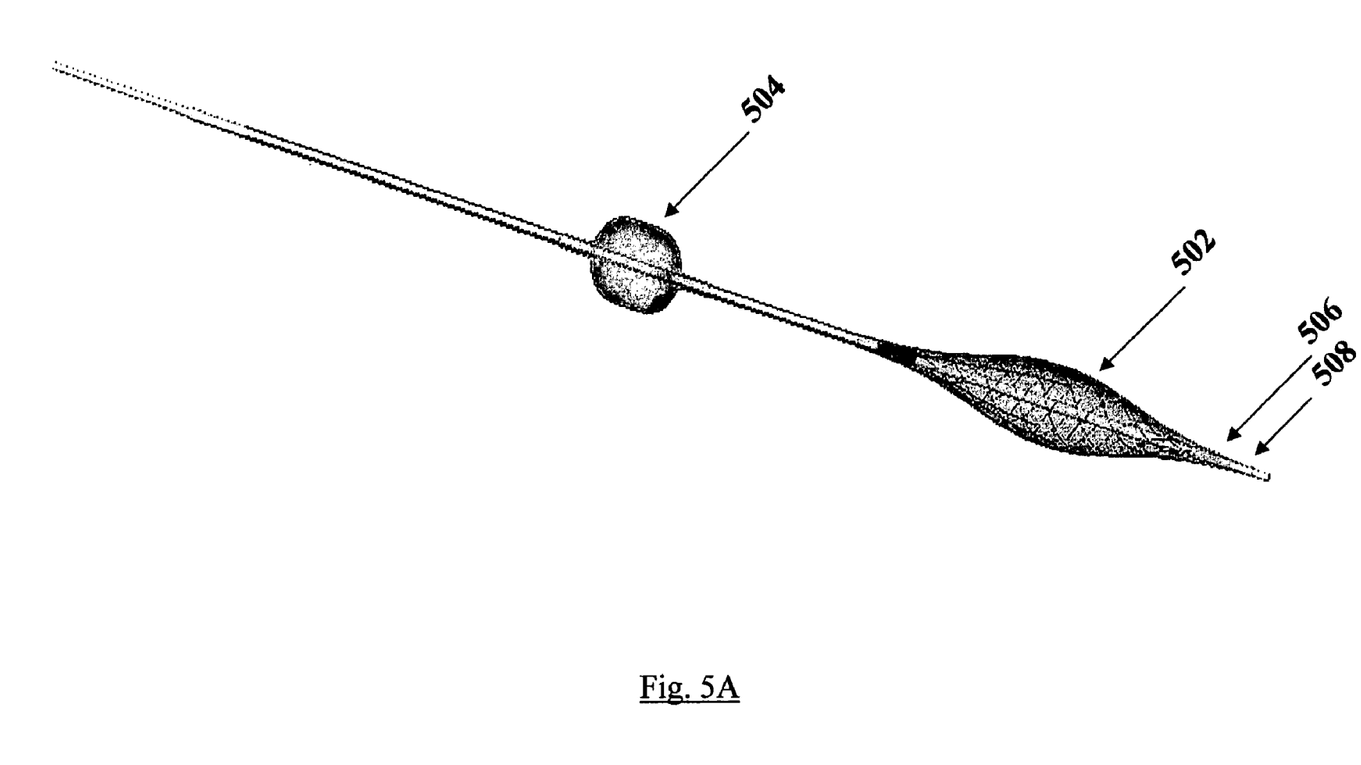
FIG. 5A is a perspective view drawing of an expandable braid catheter design and elastic sleeve covering with a separate occlusion balloon constructed in accordance with this invention.

With this in mind, an alternative embodiment of the invention utilizing a blood-flow-occluding feature was developed. FIG. 5A is a perspective view of this embodiment, which broadly includes a temperature-sensing structure 502 and an occluding component 504. Although a basket structure may be used as described in co-owned U.S. Pat. No. 6,712,771, an expandable braid design is preferred in the temperature sensing structure as it resists the tendency to twist under tortional movements and provides the other benefits outlined herein. An optional elastic cover is also preferably used over the expandable structure to provide a sealed, gas-filled backing for the sensors to further improve the accuracy of ΔT measurements by providing increased thermal insulation from the temperature of flowing blood.

Figure 5B:
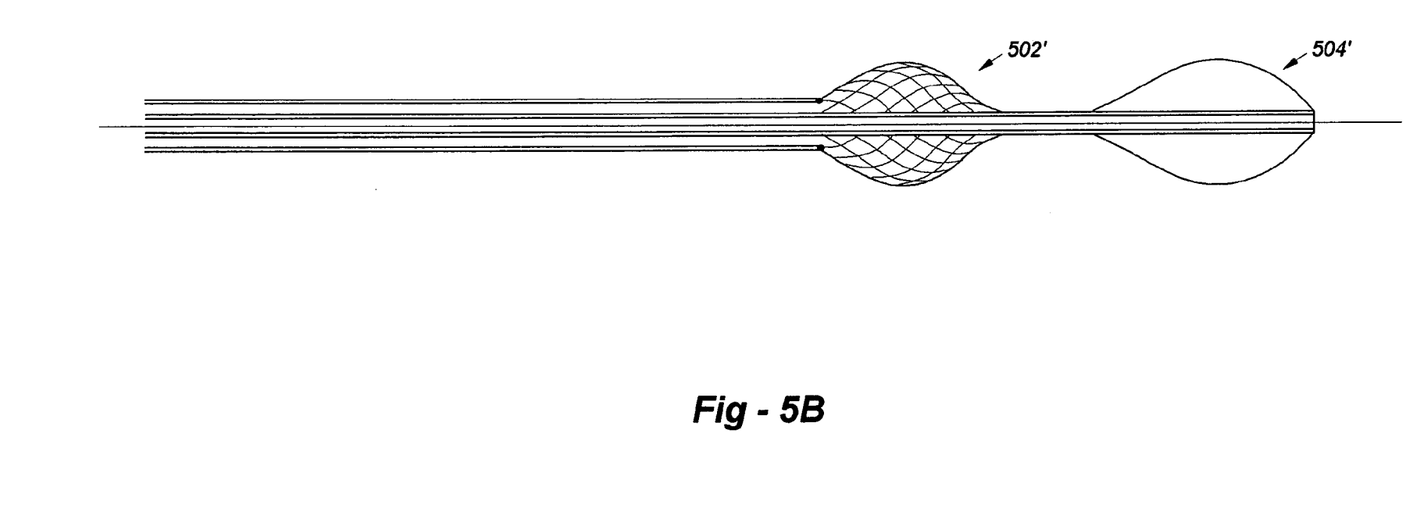
FIG. 5B illustrates how the positions of the temperature-sensing structure and occluding feature may be reversed as compared to FIG. 5A.

According to this invention, temperature sensing catheters with blood-occluding structures may be designed different ways. As shown in FIG. 5A, for example, the temperature-sensing structure 502 and occluding feature 504 may be preset at a predetermined distance from one another, such that they move in unison during repositioning. Although this limits flexibility somewhat by requiring that the occluding feature be deflated in order to reposition the temperature-sensing structure, it does simplify overall construction. Distal end 506 may either represent a connection to a central expansion control wire or a tube facilitating the use of a guidewire 508 central to the entire catheter assembly. As shown in FIG. 5B, the positions of the temperature-sensing structure 502' and occluding feature 504' may essentially be reversed.

As an alternative to fixed-distance arrangements, the temperature-sensing feature may be movable relative to the occluding feature, thereby enabling independent positioning and repositioning of the two structures. Such independent movements may also be implemented in different ways, including entirely separate occluding balloons and temperature-sensing tips, insertable and positionable side-by-side within a vessel or, alternatively, concentric structures may be used facilitating independent movement of a temperature-sensing tip relative to a proximal occluding feature (FIG. 6), or a temperature-sensing structure which is itself proximal to a more distal expandable/collapsible balloon used to occlude blood flow (FIG. 8). It will further be appreciated that a more complex structure may be implemented with proximal and distal blood-occluding balloons, all independently readjustable through appropriate combination of FIGS. 6 and 8.

Figure 6A:
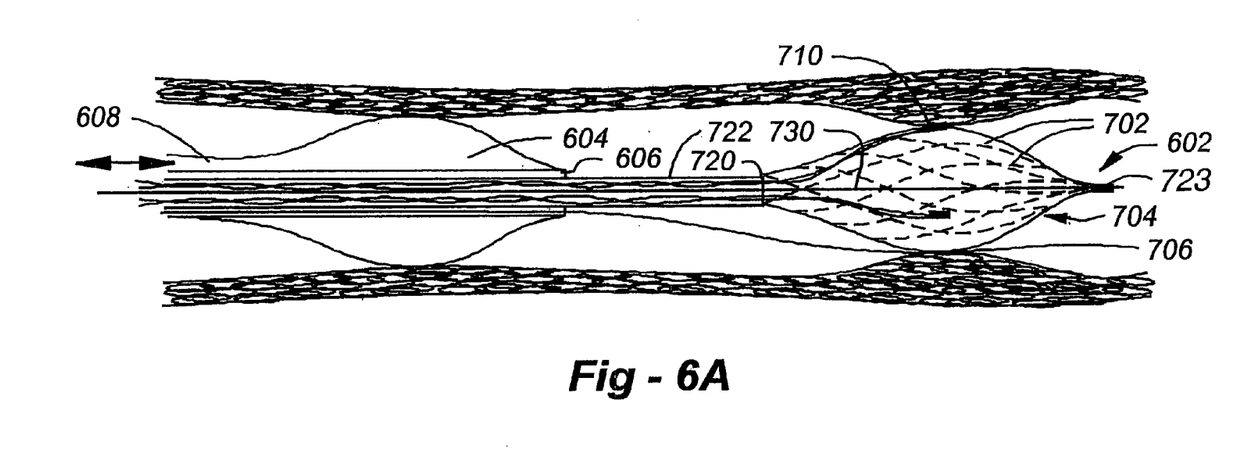
FIG. 6A is a close-up view of the alternative embodiment of the invention showing an occluding balloon and temperature-sensing structure that may be moved independently of one another.

FIG. 6A is a close-up view of a system having an occluding balloon 604 located proximally to a distal temperature-sensing structure 602, shown in an expanded state. The occlusion feature 604 is preferably in the form of a highly compliant balloon such that when it is inflated it conforms to the contour of the inside wall of the artery. A separate lumen 608 is provided to the balloon 604 for expansion and contraction utilizing air, $CO_2$ or a liquid such as saline. It is envisioned that the balloon will be inflated to a pressure just sufficient enough to occlude flow, which would be significantly less than the pressure typically used for an angioplasty. The balloon tipped portion of the catheter is tracked over a guide wire 706 which can pass through the inside lumen 606 of the balloon-tipped portion. It will be appreciated that in this and other designs according to the invention, at least one separate temperature-sensing element may be used to measure a non-wall temperature with the sensor portion in an expanded state.

Figure 6B:
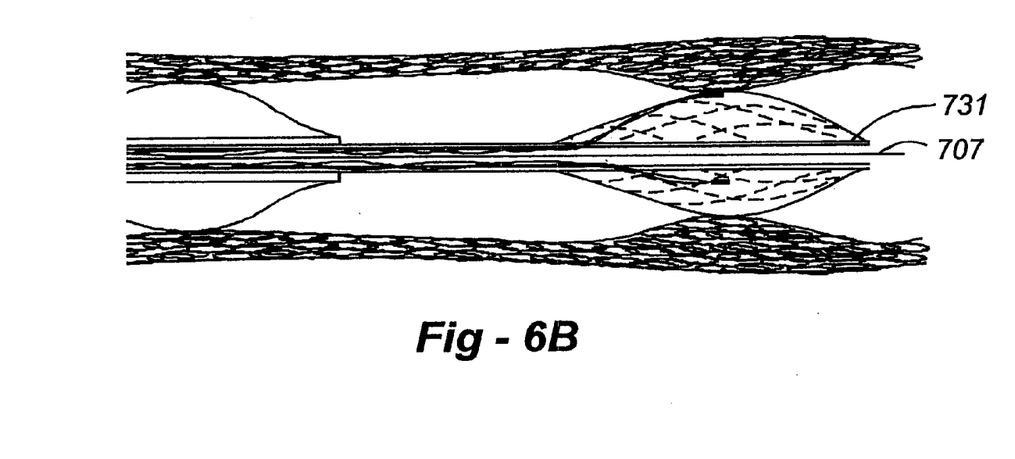
FIG. 6B shows how it may be more advantageous to utilize an inner tube to permit the use of a guidewire central to the entire catheter assembly.

The temperature sensing structure 602 includes an expandable braid 702 covered with an elastic sleeve 704 which incorporates a plurality of sensors such as 710 which communicate through wires to the proximal end of the device and data unit (not shown) located outside the patient. The elastic sleeve keeps the sensors uniformly dispersed around the circumference of the braid as it expands. It is also sealed at points 720 and 723 to keep blood from entering the space created by the expanding braid. This space will be filled with a gas, either air or some other specifically chosen gas such as $CO_2$, which will help insulate the sensor from blood temperature, allowing the sensor to yield a more accurate measurement of the artery wall temperature. Indeed, the temperature-sensing structure may be intentionally designed not to track over the guide wire, allowing it to be made with a smaller profile. In this design, the expandable braid portion is attached to a cable, or wire, on one end, and a tube 722 on its other end. The design may be further refined to incorporate a "fixed floppy-tip guide wire" extending from the tip of the control cable 730. This fixed guide wire would help the cardiologist navigate the temperature measuring portion of the catheter. As shown in FIG. 6B, it may be more advantageous to utilize an inner tube 731 as opposed to the control cable 730 to permit the use of a guidewire 707 central to the entire catheter assembly.

As will now be explained in detail, a unique and important advantage of this invention is that it allows the temperature of the vessel wall at a particular point to serve as its own temperature baseline reference. This is particularly advantageous, since it is now being understood that lesions exhibiting even slightly elevated temperatures may be representative of pathophysiology indicative of a potential adverse clinical event. According to this invention, however, by virtue of an independently controllable temperature sensing structure and occlusion feature, the temperature of a target point on a vessel wall may first be measured with blood at least partially flowing, then, with the temperature sensing structure continuing to be in an expanded position, blood flow may be partially or fully occluded with the occlusion feature to obtain a more accurate reading of $\Delta T$, defined as $\Delta T = T_{occluded} - T_{flowing}$.

This procedure is illustrated in the diagrams of FIG. 7. In FIG. 7A, a guide wire is inserted into an artery past an area containing plaque. In FIG. 7B, a structure of the type shown in FIG. 6 is journaled onto the guide wire, with the temperature sensing structure positioned relative to the plaque deposit. Note that in this embodiment and others, at least one radiopaque marker is provided on or in the expandable temperature-sensing structure, preferably in a central location to aid with fluoroscopic positioning.

Figure 7A:
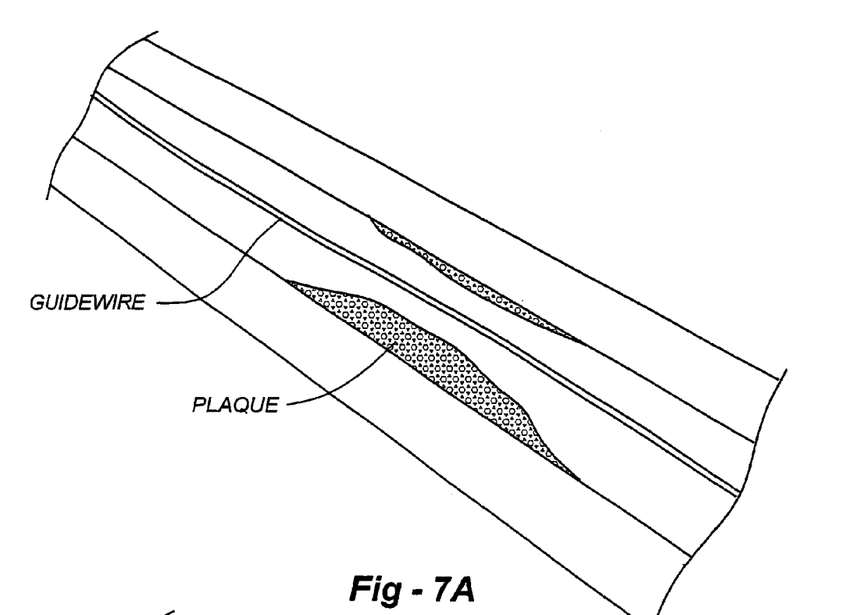
FIGS. 7A through 7I illustrate the way in which apparatus according to this invention may be used to sense particular point on a vessel wall prior to, and following, occlusion of blood flow.
Figure 7B:
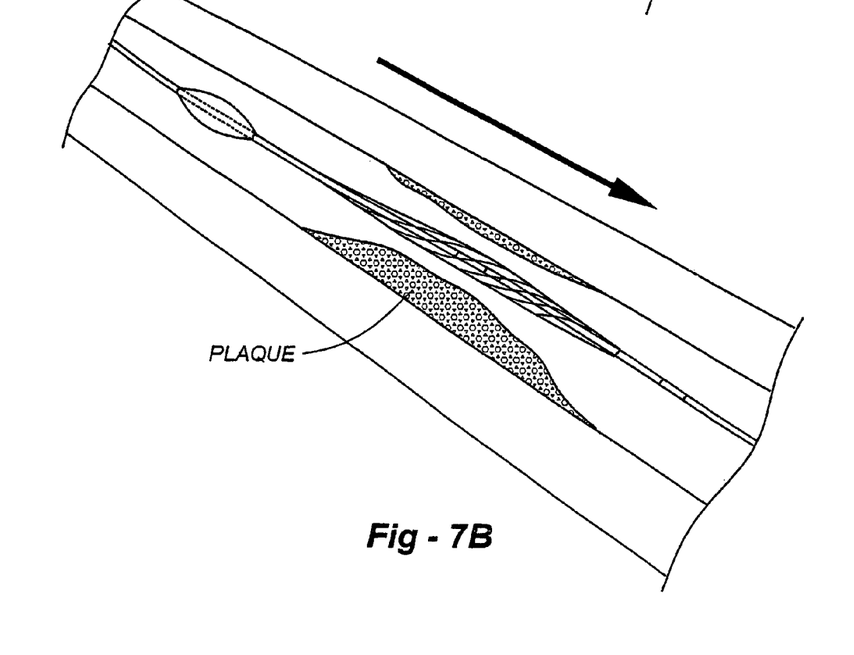
Figure 7C:
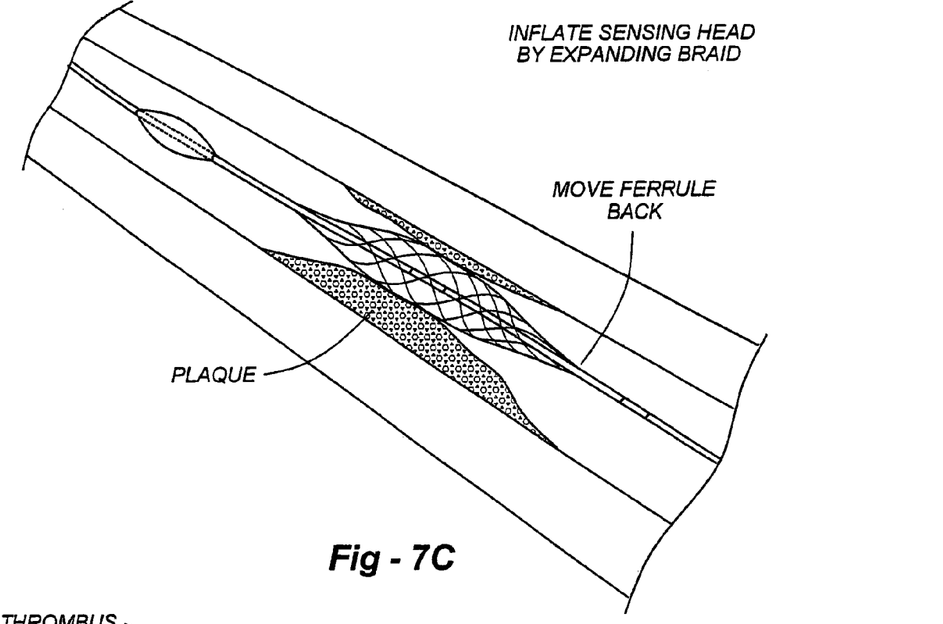
Figure 7D:
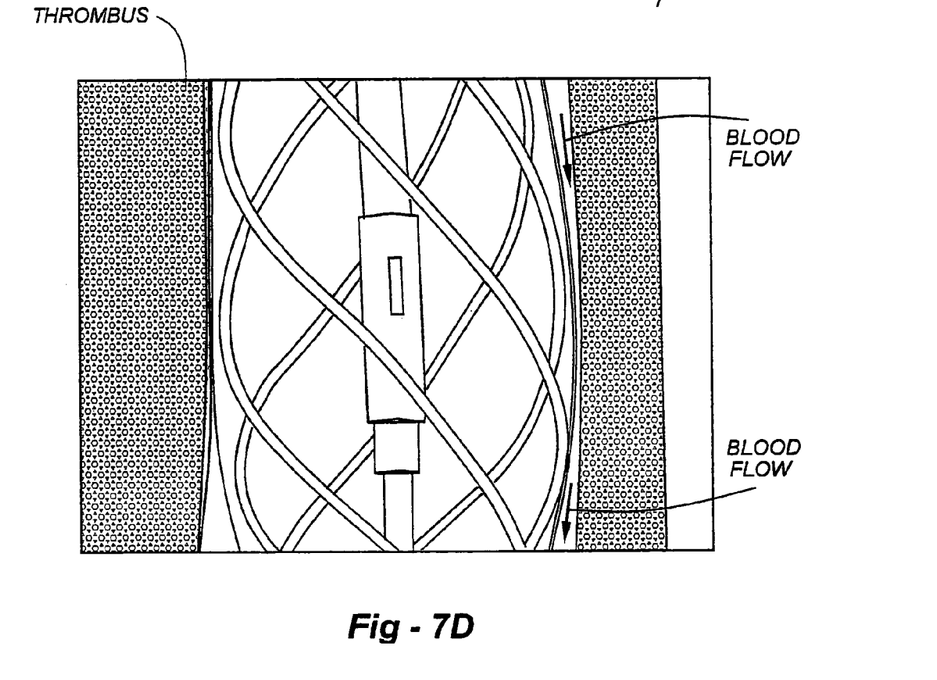
Figure 7E:
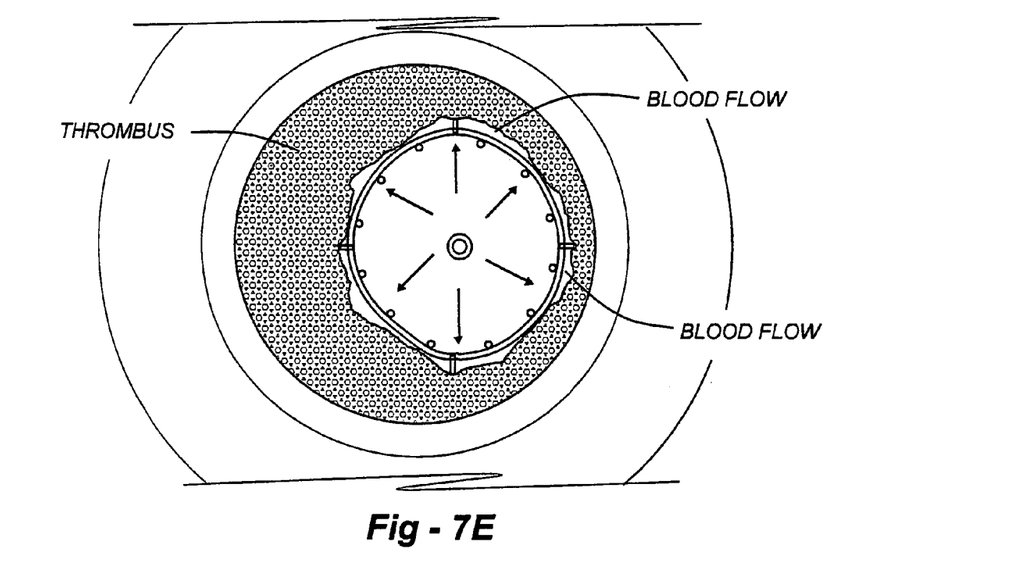

In FIG. 7C, the temperature-sensing structure is expanded by pulling back on the central control. As shown in FIG. 7D, although the expandable temperature-sensing structure may include an elastic covering effective in occluding blood flow by itself, preferably at least a slight amount of blood is permitted to flow past the temperature-sensing elements in the expanded condition. This may either be carried out with an expandable basket or braid structure without an elastic covering, or with an elastic covering designed so as to not fully occlude the vessel, at least in the areas proximate to the sensors themselves. This is shown in FIGS. 7D and 7E, with the latter being in cross-section.

Figure 7F:
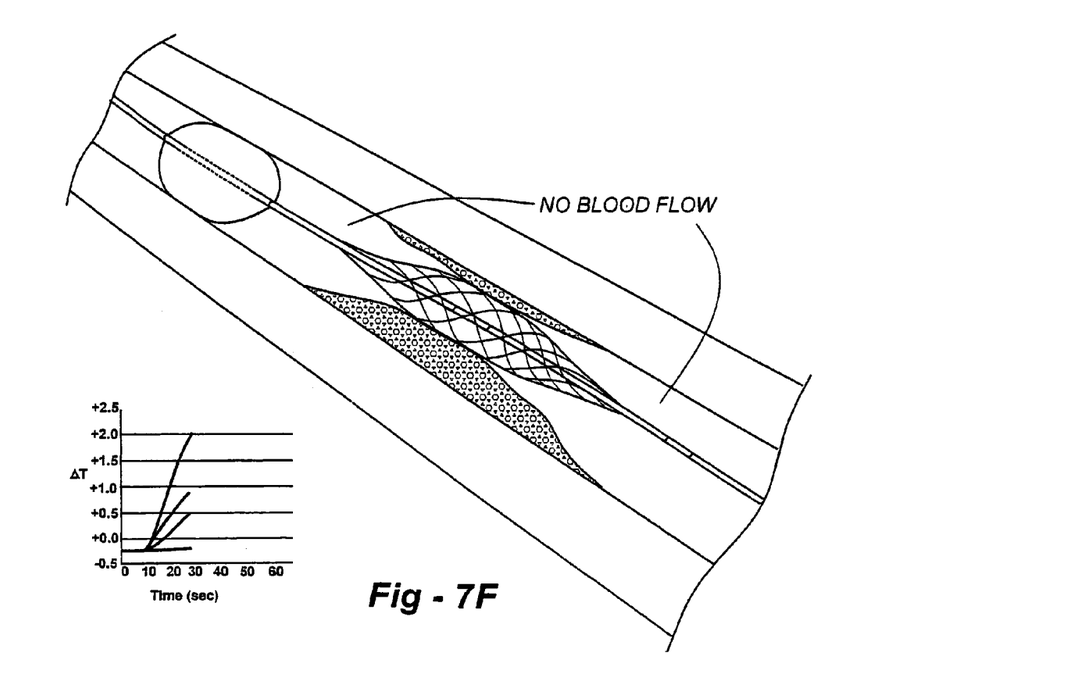
Figure 7G:
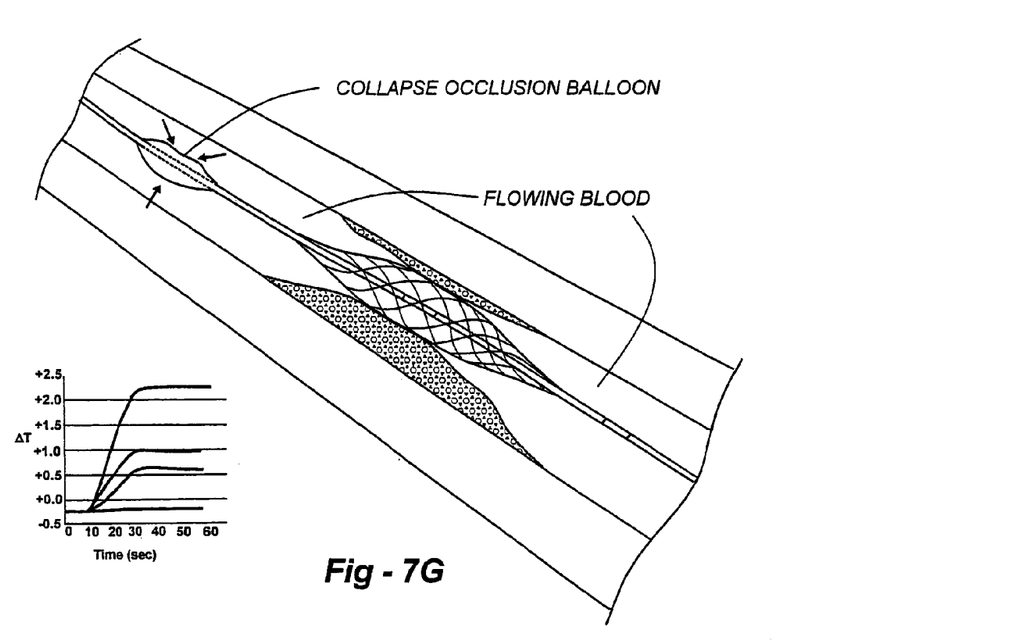
Figure 7H:
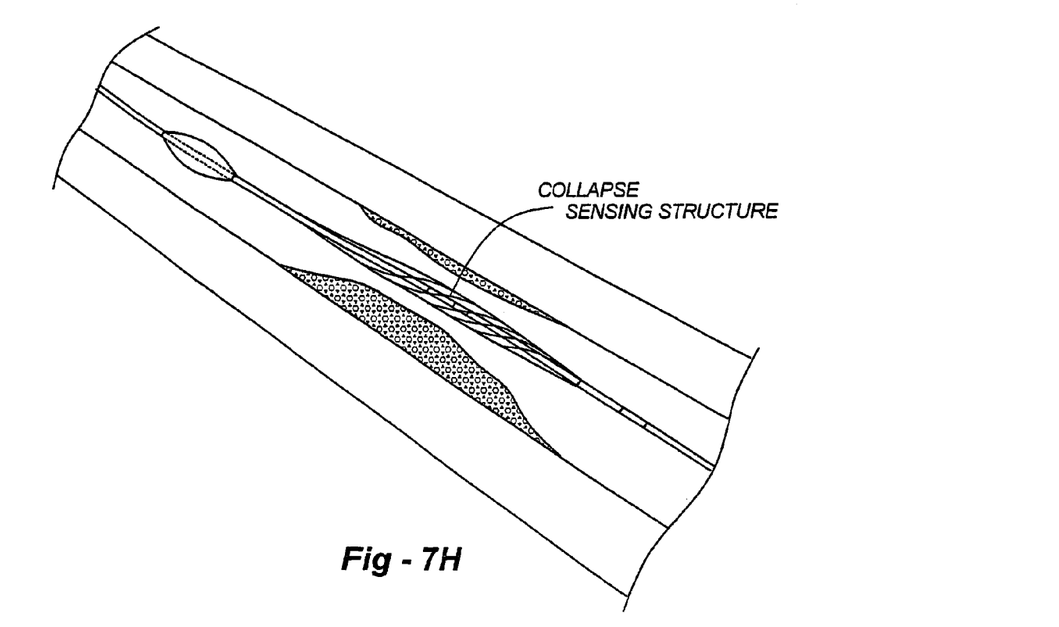
Figure 7I:
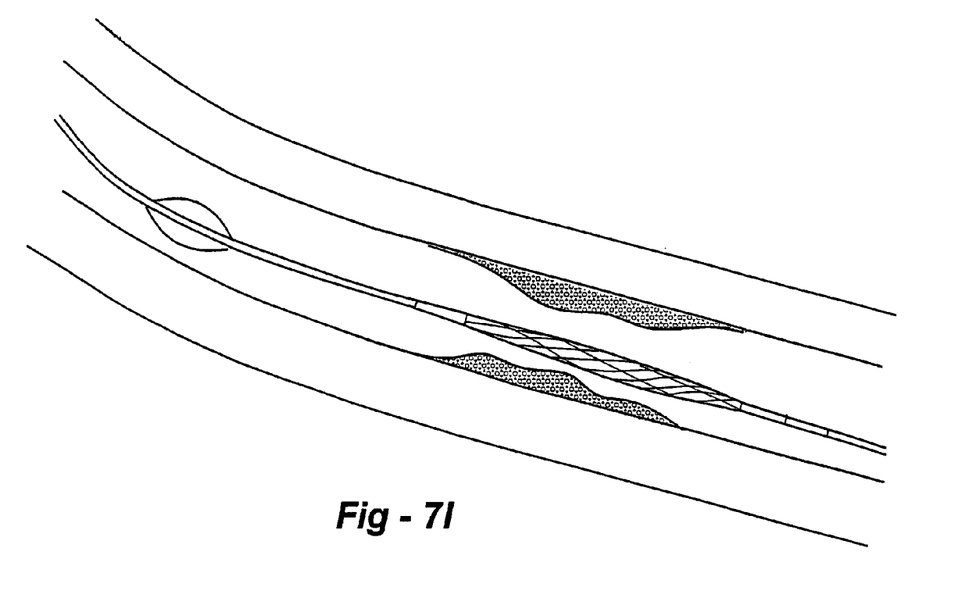

In FIG. 7F, with the temperature-sensing structure still expanded and having taken a temperature reading in a non-occluded or semi-occluded state, the occlusion feature is now expanded to fully occlude blood flow. With this arrangement, a second temperature reading is taken, enabling $\Delta T$ to be calculated as the difference between the occluded and non-occluded states.

Having taken both readings, the occluding feature is now collapsed, establishing at least low level of blood flow, after which the temperature-sensing structure is collapsed, enabling the assembly to be removed from the body or repositioned to a different location. It will be appreciated that the procedure just described may be carried out with any of the blood-occluding embodiments disclosed herein, whether the sensors and occluding balloon are fixed at a predetermined distance or movable to one another.

Figure 8A:
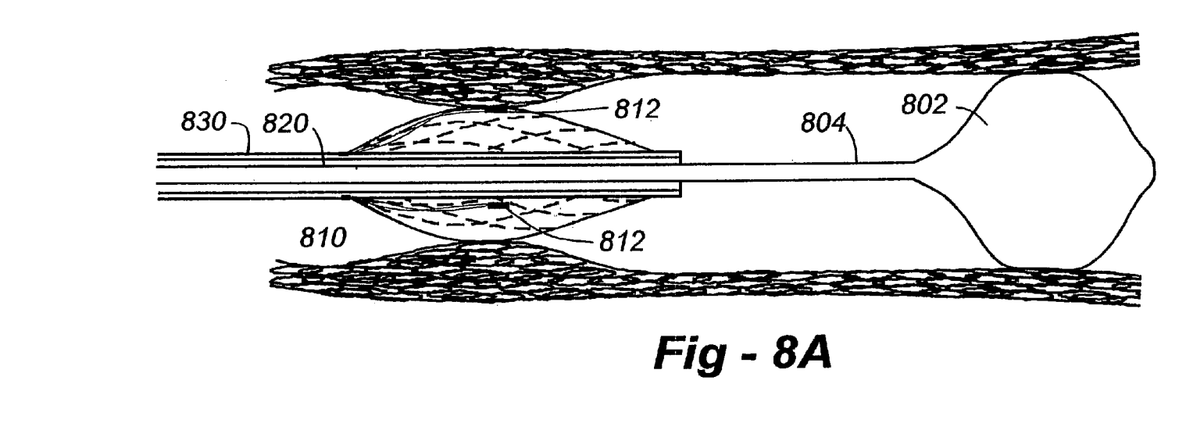
FIG. 8A is a drawing which shows one way in which a separate occluding balloon may be positioned distally as opposed to proximally of an expandable/collapsible temperature-sensing structure.
Figure 8B:
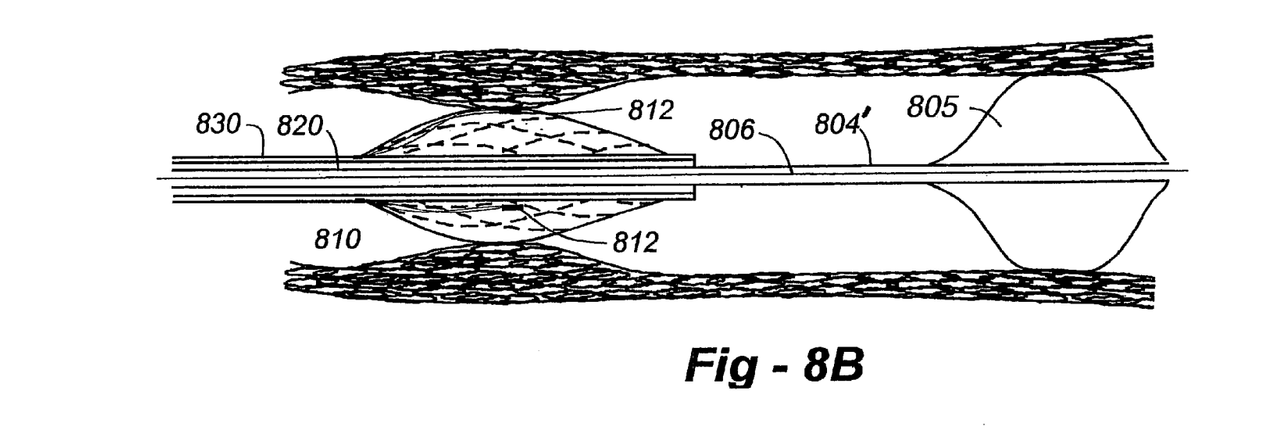
FIG. 8B shows how a tube may be extended to the distal end of a device such as that shown in FIG. 8A, facilitating the use of a central guidewire.

FIG. 8 illustrates an alternative embodiment of the invention, wherein the occluding feature 802 is located distally with respect to the temperature-sensing structure 810 having sensors 812. In this case, three elongated cannula are used, including a central tube 804 to inflate and deflate the balloon 802, the tube 820 sealed distally to the temperature-sensing structure 810 and tube 830 sealed to the proximal end of the temperature-sensing structure 810. Through the use of concentric tube 820 and 830 configured concentrically with one in the other, the temperature-sensing structure 810 may be expanded by pulling on tube 820 with 830 fixed; pushing on tube 830 with 820 fixed; or simultaneously pulling on tube 820 with pushing on tube 830. The temperature-sensing structure 810 may be collapsed by pushing on tube 820 with 830 fixed; pulling on tube 830 with 820 fixed, or simultaneously pushing 820 while pulling on tube 830. As shown in FIG. 8B, tube 804 may be extended to the distal end of the device as 804', facilitating the use of a central guidewire 806. Tube 804' would need to be a multi-lumen tube to provide a path for inflating/deflating balloon 805.

We claim:

1. A catheter assembly for sensing the temperature of a blood vessel wall, comprising:
    an outer tube having a proximal end intended to remain outside a patient and a distal end terminating in an inflatable balloon to occlude blood flow;
    an inner tube disposed co-extensively within the outer tube, the inner tube extending to a distal tip beyond the distal end of the outer tube;
    a central elongate member comprising a tube to receive a guidewire;
    an expandable basket or braid structure having a first end attached to the distal tip of the inner tube and a second end attached to the central elongate member slidingly disposed within the inner tube to an expansion control at the proximal end;
    the expandable basket or braid structure including one or more temperature sensors supported thereon, each sensor being operative to generate an electrical signal indicative of temperature, such that operation of the control causes the structure to move between a collapsed state, enabling at least one of the sensors to be positioned in a section of the vessel to be measured, and an expanded state, wherein at least one of the sensors is in contact with, or immediately proximate to, the vessel wall before and after blood flow is occluded; and
    at least one sensor for measuring a non-wall temperature.

2. The catheter assembly of claim 1, further including an elastic sleeve covering the expandable basket or braid structure.

3. The catheter assembly of claim 1, wherein the temperature sensors are thermistors.

4. The catheter assembly of claim 1, further including a data unit operative to receive signals from the temperature sensors and display information indicative of vessel wall temperature.

5. The catheter assembly of claim 4, wherein temperature sensors are individually hardwired to the data unit.

6. The catheter assembly of claim 4, wherein temperature sensors are multiplexed to the data unit.

7. The catheter assembly of claim 1, wherein the catheter assembly is disposable.

* * * * *